United States Patent [19]
Klaras et al.

[11] Patent Number: 5,703,691
[45] Date of Patent: Dec. 30, 1997

[54] INTEGRATED DETECTOR FOR LASER REMOTE SENSORS

[75] Inventors: Louis F. Klaras, Redondo Beach; David B. Cohn, Torrance, both of Calif.

[73] Assignee: Hughes Electronics, Los Angeles, Calif.

[21] Appl. No.: 610,903

[22] Filed: Mar. 5, 1996

Related U.S. Application Data

[63] Continuation of Ser. No. 496,739, Jun. 29, 1995, abandoned, which is a continuation of Ser. No. 164,593, Dec. 9, 1993, abandoned.

[51] Int. Cl.$^6$ .................................................. G01N 21/61
[52] U.S. Cl. ........................... 356/437; 356/236; 356/434
[58] Field of Search ............................... 356/437, 236, 356/434; 250/338.5, 339.13, 228

[56] References Cited

U.S. PATENT DOCUMENTS

| | | | |
|---|---|---|---|
| 1,950,975 | 3/1934 | Davis | 356/236 |
| 4,061,918 | 12/1977 | Preier et al. | 250/343 |
| 4,770,530 | 9/1988 | Van Aken et al. | 356/448 |

FOREIGN PATENT DOCUMENTS

| | | | |
|---|---|---|---|
| 56-47734 | 4/1981 | Japan | 356/437 |

OTHER PUBLICATIONS

Ben-David et al. "High Pulse Repetition Frequency, Multiple Wavelength, Pulsed CO2 Lidar System for Atmospheric Transmission and Target Reflectance Measurements".
DE-A-28 34 983 (Blazek).
Dennis "Infra-Red Lasers and Their Use in Atmospheric Pollution Monitoring".

*Primary Examiner*—Richard A. Rosenberger
*Attorney, Agent, or Firm*—G. R. Lindeen III; W. K. Denson-Low

[57] ABSTRACT

A remote laser sensor incorporating a single integrated detector. The laser sensor comprises a laser for transmitting laser energy that is applied to a target, and a beamsplitter for sampling of the transmitted laser energy. A telescope is provided for collecting laser energy reflected from the target. The integrated detector comprises an integrating sphere for receiving the sampled transmitted laser energy and for receiving the laser energy reflected from the target, and a detector coupled to the integrating sphere for selectively detecting the sampled transmitted laser energy and the laser energy reflected from the target. A scatter plate may be disposed inside the integrating sphere for preventing photons from entering the detector that result directly from a first scattering event within the sphere. In operation, the laser provides a transmit beam that is directed at the target and reflected energy from the target is collected by the telescope and focused onto the detector. Detector integration is accomplished by using a single detector chip mounted to a rear surface of the integrating sphere, which allows sampling of the entire cross-section of the laser transmit beam. The beamsplitter is employed to sample a portion of the transmit beam which is applied to the detector.

13 Claims, 1 Drawing Sheet

INTEGRATED DETECTOR FOR LASER REMOTE SENSORS

This is a continuation application Ser. No. 08/496,739 filed Jun. 29, 1995, now abandoned, which is a continuation of application Ser. No. 08/164,593, filed Dec. 9, 1993, now abandoned.

BACKGROUND

The present invention relates to laser sensors, and more particularly, to an improved remote laser sensor incorporating an integrated detector.

The design of laser sensors used for remote detection of chemicals are based on a well-known differential absorption lidar (DIAL) approach. Laser sensors for remote chemical detection typically use two detectors, one to monitor the transmit beam and one to monitor the received beam. Measurement normalization is performed by taking the ratio of the two signals. The conventional two-detector systems suffer from significant calibration problems related to (1) differing detector sensitivity as a function of wavelength, (2) differing pulse frequency response, and (3) sensitivity changes over time. In the simplest case, the sensor transmits two pulses, each at a different wavelength, and compares the returns. One wavelength is tuned to the peak of an absorption band of the chemical and the other wavelength is tuned for no absorption. In practice however, the laser transmits different energies at different wavelengths, and even for a single wavelength, the output can vary from pulse to pulse.

Therefore, it is necessary to use a transmit detector to measure the laser output pulse for each return pulse and to normalize the pulse returns. Normalization is performed by taking the ratio of the return pulse to the transmit pulse at a single wavelength (receive/transmit). The problem is that the transmit and receive detectors have different responsivities as a function of wavelength and different bandwidths so that pulse shape is also effected. Furthermore, these responsivities change over time so that recalibration of the sensor is recommended at each service event.

Sensors using pulsed infrared lasers for remote detection of chemicals perform their function by transmitting a number of wavelengths in sequence and comparing the backscattered signals collected by a telescope. These sensors typically use two detectors, one to monitor the transmit laser pulse and one to measure the return signal at the focus of the telescope. It is essential to normalize the return signals with the transmit pulse because laser output energy can change by as much as 50 percent from wavelength to wavelength and by as much as 10 percent from pulse to pulse for a single wavelength. Sensor calibration depends upon precise measurement of the transmit and receive detector sensitivity as a function of wavelength and upon the detector frequency response. In addition, detectors are known to change characteristics over time, so that periodic recalibration is necessary. Detector characteristics may vary by as much as 20 percent and the typical sensor is required to operate with a noise floor of 1-2 percent. Therefore, sensor calibration as a function of wavelength is the determining factor in sensor performance. The opto-mechanical and electronic complexity of a two-detector sensor imposes severe limitations on the sensor design. The material and labor cost of incorporating two detectors is more than may be desirable for many applications.

Therefore, it is an objective of the present invention to provide laser sensor apparatus that eliminates the use of separate transmit and receive detectors and performs output monitor and receive detection functions using a single detector.

SUMMARY OF THE INVENTION

In order to meet the above and other objectives, the present invention is an improved laser sensor incorporating a single integrated detector. More specifically, the present invention comprises laser sensor apparatus that includes a laser for transmitting laser energy that is applied to a target, and a beamsplitter for sampling of the transmitted laser energy. A telescope is provided for collecting laser energy reflected from the target. An integrated detector is provided that comprises an integrating sphere for receiving the sampled transmitted laser energy and for receiving the laser energy reflected from the target, and a detector coupled to the integrating sphere for selectively detecting the sampled transmitted laser energy and the laser energy reflected from the target. A scatter plate may be disposed inside the integrating sphere for preventing photons from entering the detector that result directly from a first scattering event within the sphere.

In operation, the laser provides a transmit beam that is directed at the target and reflected energy from the target is collected by the telescope and focused onto the detector. The beamsplitter is employed to sample a portion of the transmit beam that is applied to the detector. Detector integration is accomplished by using a single detector chip mounted to a rear surface of the integrating sphere, which allows sampling of the entire cross-section of the laser transmit beam.

The present invention eliminates problems relating to calibration of conventional sensors by using a single detector to monitor the laser transmit and return pulses instead of two conventional detectors, thereby greatly simplifying sensor optics and electronics and eliminating the above-cited calibration problems. Furthermore, the sensor design is greatly simplified, and its cost is reduced by eliminating the need for a separate transmit detector, its preamplifier, temperature control circuitry, and optics.

The present invention may be used in chemical detection and monitoring equipment, or pollution monitoring equipment, for example. Use of the present integrated detector in such equipment helps to reduce the cost of the sensor and make the sensor equipment more affordable.

BRIEF DESCRIPTION OF THE DRAWINGS

The various features and advantages of the present invention may be more readily understood with reference to the following detailed description taken in conjunction with the accompanying drawings, wherein like reference numerals designate like structural elements, and in which.

DETAILED DESCRIPTION

Figure 1:
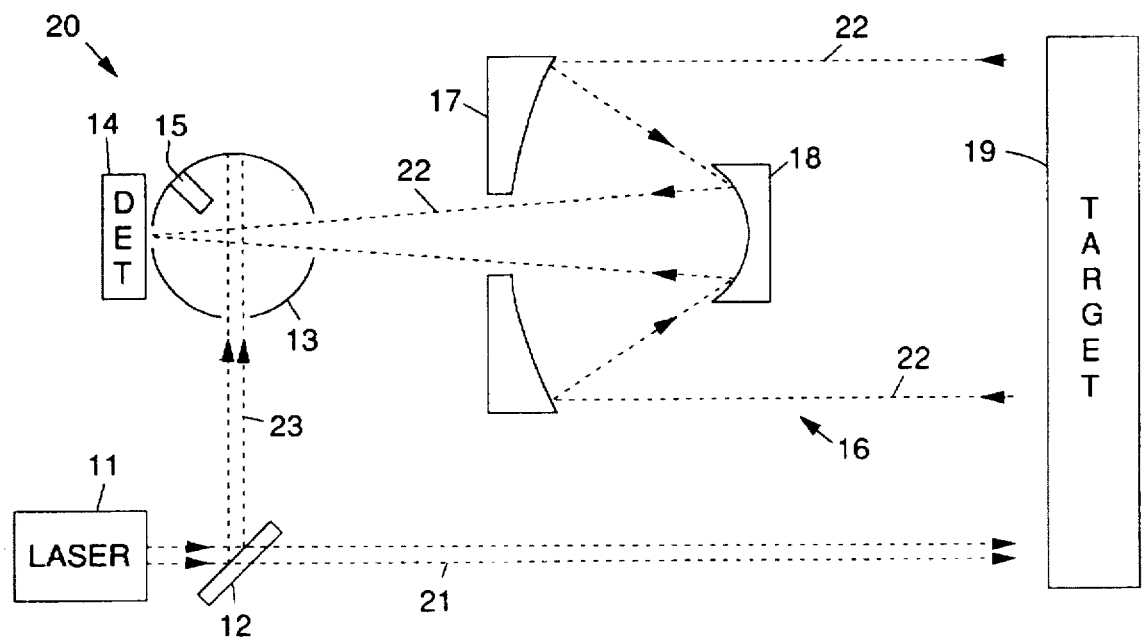
FIG. 1 illustrates a cross-sectional view of laser sensor apparatus incorporating an integrated detector in accordance with the principles of the present invention.

Referring to the drawing figures, FIG. 1 illustrates a cross-sectional view of laser sensor apparatus 10 incorporating an integrated detector 20 in accordance with the principles of the present invention. A typical sensor transmit and receive optical train of the laser sensor apparatus 10 is shown in FIG. 1. A laser 11, such as a $CO_2$ TEA laser, for example, is provided and a beamsplitter 12 directs a small fraction of its transmit pulse 21 or beam 21 to an integrated detector 20 in accordance with the present invention. The integrated detector 20 comprises an integrating sphere 13 and a single integrated detector 14 mounted to a rear surface 13a of the integrating sphere 13. The beamsplitter 12 may be comprised of an uncoated zinc selenide (ZnSe) plate, for example, oriented at Brewster's angle with respect to the transmit pulse 21 from the laser 11. The integrating sphere 13 provides for uniform sampling of the entire cross-section of the transmit pulse 21. Uniform sampling is a critical function, because the laser transmit pulse 21 is spatially highly multi-mode with intensity peaks that may exceed the average by 50 percent. The major portion of the transmit pulse 21 is directed to a target 19. A return pulse 22 or beam 22 from the target 19 is collected by a telescope 16 and focused directly onto the detector 14 in a conventional manner. The telescope 16 is comprised of a primary reflector 17 and a secondary reflector 18, such as is known in the art.

The $CO_2$ TEA laser 11 is typically used in remote chemical sensors, for example, and it emits a transmit pulse 21 comprised of a 150–200 nanosecond long spike, for example, followed by a 1 microsecond tail. In the case of the single integrated detector 20 of the present invention, which sequentially measures transmit and receive pulses 21, 22 as is described herein, the tail of the transmit pulse 21 obscures signals from the return pulse 22 for about 1 microsecond. This corresponds to a range of about 150 meters. Chemical sensors are typically used at ranges of from 500 meters to 3 kilometers so that a loss of capability for the close-in 150 meter range poses no problem.

Figure 2:
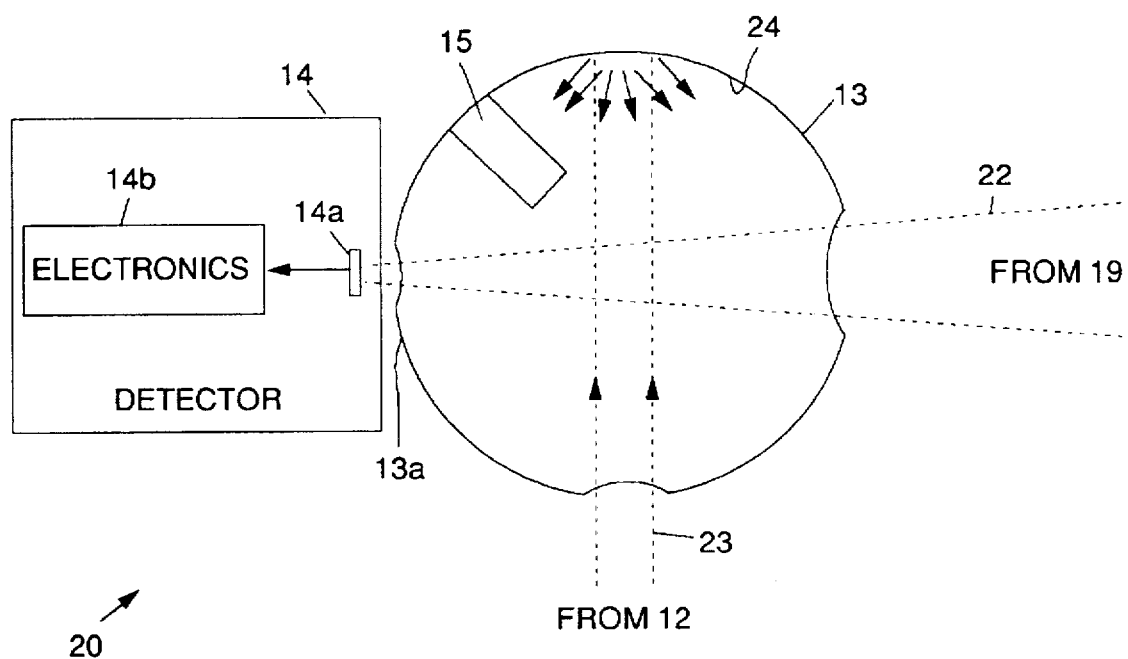
FIG. 2 illustrates details of the integrated detector of the present invention used in the laser sensor apparatus of FIG. 1.

FIG. 2 illustrates details of the integrated detector 20 of the present invention used in the laser sensor apparatus 10 of FIG. 1. The integrated detector 20 includes a detector chip 14a and detector electronics, 14b, both of which are generally well known in the art. A scatter plate 15 is disposed within the integrating sphere 13.

The transmit beam 21 enters the integrating sphere 13 and scatters off its internal wall 24. This spatially randomizes the input flux of the return pulse 22 to fill the sphere 13 uniformly, and the detector 14 (detector chip 14a) samples the randomized transmit beam 21. The scatter plate 15 is used to prevent photons from entering the detector 14 (detector chip 14) that result directly from a first scattering event. The return pulse 22 is focused directly on the detector chip 14a. The field of view of the telescope 16, the focal length of the telescope 16, and the size of the detector chip 14a are related in a well-known conventional way, and are designed in a conventional manner to cooperate together.

In operation, the the integrated detector 20 is used to measure the energy of the laser transmit pulse 21 and its associated return pulse 22 and normalize the pulse returns. Normalization is performed by taking the ratio of the energy in the return pulse 22 to the energy in the transmit pulse 21 at a single wavelength. By using the integrated detector 20, there is no problem regarding responsivity as a function of wavelength or different bandwidths because of the use of a single detector chip 14a. Furthermore, even though the responsivity of the single detector chip 14a may change over time, it is not necessary to recalibrate the laser sensor apparatus 10.

The amplitudes of the transmit and receive pulses 21, 22 are measured sequentially in time using the integrated detector 20 comprising the single detector 14a and the integrating sphere 13. For typical chemical detection laser sensor apparatus 10, for example, the laser transmit pulse 21 is comprised of a spike that is 150–200 nanoseconds in duration, followed by a tail of about 1 microsecond duration. Because of its proximity to the detector 14, the sampled portion of the transmit pulse 21 is measured instantaneously by the detector 14. The receive pulse 22, however, arrives at the detector 14 typically on the order of 10 microseconds later because of the pulse time-of-flight to the target 19 and back. Therefore, the transmit and receive pulses 21, 22 do not interfere in time and the single detector 14 is effectively time-multiplexed.

Experiments were performed with a 2 inch diameter integrating sphere 13 and liquid nitrogen cooled mercury cadmium telluride (HgCdTe) detector 14. A $CO_2$ TEA laser 11 operated at a pulse output energy of 150 mJ. The beamsplitter 13 was comprised of an uncoated zinc selenide (ZnSe) plate oriented at Brewster's angle relative to the laser transmit beam 21. It was found that the integrated detector 20 worked well in detecting the energy transmitted by the laser 11 and energy reflected and received from the target 19.

Thus there has been described a new and improved remote laser sensor incorporating an integrated detector. It is to be understood that the above-described embodiment is merely illustrative of some of the many specific embodiments which represent applications of the principles of the present invention. Clearly, numerous and other arrangements can be readily devised by those skilled in the art without departing from the scope of the invention.

What is claimed is:

1. A remote laser sensor apparatus comprising:

a pulsed laser for transmitting a pulse of laser energy at a predetermined wavelength;

a beamsplitter for directing respective portions of the pulse of laser energy along a first path and a second path, the first path directing the pulse of laser energy toward a target;

a telescope for collecting and focusing a reflected portion of the pulse of laser energy having been reflected from the target;

a single detector system comprising an integrating sphere, the integrating sphere directing the reflected portion of the pulse of laser energy having been collected and focused and the respective portion of the pulse of laser energy having been directed along the second path into a single optical path, and a single detector coupled to the single optical path for serially detecting the reflected portion of the pulse of laser energy and the respective portion of the pulse of laser energy having been directed along the second path, the pulse of laser energy having a prescribed pulse duration, the first path having a first prescribed path length and the second path having a second prescribed path length such that serial detection of the reflected portion of the pulse of laser energy and the respective portion of the pulse of laser energy having been directed along the second path is achieved.

2. The laser sensor apparatus of claim 1 wherein the laser comprises a CO2 TEA laser.

3. The apparatus of claim 1 further comprising a scatter plate disposed inside said integrating sphere.

4. The apparatus of claim 1 wherein said integrating sphere has a front surface and a rear surface, the front surface receiving said reflected portion of the pulse of laser energy.

5. The apparatus of claim 1 wherein said detector further comprises single channel electronics processing.

6. A remote laser sensor apparatus that includes a pulsed laser for transmitting a pulse of laser energy at a predetermined wavelength, a beamsplitter for directing respective portions of the pulse of laser energy along a first path and a second path, the first path directing the respective portion of the pulse of laser energy having directed along the first path toward a target, and a telescope for collecting and focusing a reflected portion of the pulse of laser energy reflected from the target, wherein the improvement comprises:

a detector system comprising;

an integrating sphere, the integrating sphere directing the reflected portion of the pulse of laser energy having been collected and focused and the respective portion of the pulse of laser energy having been directed along the second path into a single optical path; and a single detector coupled to the single optical path for serially detecting the reflected portion of the pulse of laser energy and the respective portion of the pulse of laser energy having been directed along the second path, the pulse of laser energy having a prescribed pulse duration, the first path having a first prescribed path length, and the second path having a second prescribed path length such that serial detection of the reflected portion of the pulse of laser energy and the respective portion of the pulse of laser energy having been directed along the second path is achieved.

7. The laser sensor apparatus of claim 6 wherein the laser comprises a CO2 TEA laser.

8. The apparatus of claim 6 further comprising a scatter plate disposed inside said integrating sphere.

9. The apparatus of claim 6 wherein said detector further comprises single channel electronics processing.

10. Laser sensor apparatus comprising:

a laser;

a beamsplitter for splitting an output pulse from the laser into a first pulse and a second pulse:

optics adapted to collect and focus the second pulse after reflection;

an integrating sphere adapted to serially receive the first pulse from the beamsplitter and the reflected second pulse from the optics, the integrating sphere directing the first pulse and the reflected second pulse into a single optical path, the output pulse having a prescribed pulse duration, and the first pulse following a first path of a first prescribed length, and the second pulse following a second path of a second prescribed length such that separate-in-time direction of the first pulse and the second pulse into the single optical path is achieved; and a single detector coupled with the integrating sphere and adapted to serially detect the first pulse and the reflected second pulse, having been directed separately-in-time into the single optical path by the integrating sphere.

11. The apparatus of claim 10, wherein the laser comprises a CO2 TEA laser.

12. The apparatus of claim 10 further comprising a scatter plate disposed inside said integrating sphere.

13. The apparatus of claim 10 wherein said detector further comprises single channel electronics processing.

* * * * *